United States Patent
Petermann et al.

(10) Patent No.: US 10,377,835 B2
(45) Date of Patent: Aug. 13, 2019

(54) WATER-SOLUBLE ESTERIFIED CELLULOSE ETHERS

(71) Applicant: Dow Global Technologies LLC, Midland, MI (US)

(72) Inventors: Oliver Petermann, Hamburg (DE); Matthias Knarr, Nienburg/Weser (DE)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 15/550,094

(22) PCT Filed: Mar. 8, 2016

(86) PCT No.: PCT/US2016/021318
§ 371 (c)(1),
(2) Date: Aug. 10, 2017

(87) PCT Pub. No.: WO2016/148973
PCT Pub. Date: Sep. 22, 2016

(65) Prior Publication Data
US 2018/0072818 A1    Mar. 15, 2018

Related U.S. Application Data

(60) Provisional application No. 62/133,508, filed on Mar. 16, 2015.

(51) Int. Cl.
| | | |
|---|---|---|
| C08B 13/00 | (2006.01) | |
| A61K 47/38 | (2006.01) | |
| C09D 101/32 | (2006.01) | |
| C08L 1/32 | (2006.01) | |
| A23P 20/10 | (2016.01) | |
| A61K 9/48 | (2006.01) | |
| A23P 10/30 | (2016.01) | |

(52) U.S. Cl.
CPC .............. *C08B 13/00* (2013.01); *A23P 10/30* (2016.08); *A23P 20/105* (2016.08); *A61K 9/4816* (2013.01); *A61K 9/4833* (2013.01); *A61K 9/4866* (2013.01); *A61K 47/38* (2013.01); *C08L 1/32* (2013.01); *C09D 101/32* (2013.01)

(58) Field of Classification Search
CPC combination set(s) only.
See application file for complete search history.

(56) References Cited

U.S. PATENT DOCUMENTS

| | | |
|---|---|---|
| 3,435,027 A | 3/1969 | Armand et al. |
| 4,226,981 A | 10/1980 | Onda et al. |
| 4,365,060 A | 12/1982 | Onda et al. |
| 2012/0161364 A1 | 6/2012 | Son et al. |

FOREIGN PATENT DOCUMENTS

| | | |
|---|---|---|
| EP | 0219426 | 4/1987 |
| WO | 2005115330 | 12/2005 |
| WO | 2011159626 A1 | 12/2011 |
| WO | 2013148154 A1 | 10/2013 |
| WO | 2013164121 A1 | 11/2013 |
| WO | 2014031422 A1 | 2/2014 |
| WO | 2014137777 A1 | 9/2014 |
| WO | 2014137778 A1 | 9/2014 |

OTHER PUBLICATIONS

Fukasawa, M. et al. "Molecular Weight Determination of Hypromellose Acetate Succinate (HPMCAS) Using Size Exclusion Chromatography with a Multi-Angle Laser Light Scattering Detector" Chem. Pharm. Bull. 2004, 52(11) 1391-1393 (Year: 2004)*
McGinity, J.W. "Aqueous Polymeric Coatings for Pharmaceutical Dosage Forms" The University of Texas at Austin, 1989, pp. 105-112 (Year: 1989)*
McGinity, Aqueous Polymeric Coatings for Pharmaceutical Dosage Forms, The University of Texas at Austin, 1989.
Rowe et al., Handbook of Pharmaceutical Excipients, 6th edition, Pharmaceutical Press, 2010.
AQOAT, Shin-Etsu Chemical Co. Ltd.

\* cited by examiner

*Primary Examiner* — Andrew S Rosenthal
(74) *Attorney, Agent, or Firm* — Ballard Spahr LLP

(57) ABSTRACT

1. An esterified cellulose ether which i) comprises groups of the formula —C(O)—R—COOH or a combination of aliphatic monovalent acyl groups and groups of the formula —C(O)—R—COOH, wherein R is a divalent hydrocarbon group, ii) has a weight average molecular weight $M_w$ of up to 70,000 Dalton, iii) has a degree of neutralization of the groups —C(O)—R—COOH of not more than 0.4, and iv) has a solubility in water of at least 2.0 weight percent at 2° C., is useful for preparing enteric capsules.

14 Claims, 1 Drawing Sheet

WATER-SOLUBLE ESTERIFIED CELLULOSE ETHERS

FIELD

This invention concerns novel esterified cellulose ethers and their use for producing coatings and capsule shells.

INTRODUCTION

Esters of cellulose ethers, their uses and processes for preparing them are generally known in the art. When the esterified cellulose ethers comprise ester groups which carry carboxylic groups, the solubility of the esterified cellulose ethers in aqueous liquids is typically dependent on the pH. For example, the solubility of hydroxypropyl methyl cellulose acetate succinate (HPMCAS) in aqueous liquids is pH-dependent due to the presence of succinate groups, also called succinyl groups or succinoyl groups. HPMCAS is known as enteric polymer for pharmaceutical dosage forms. In the acidic environment of the stomach HPMCAS is protonated and therefore insoluble. HPMCAS undergoes deprotonation and becomes soluble in the small intestine, which is an environment of higher pH. The pH-dependent solubility is dependent on the degree of substitution of acidic functional groups. The dissolution time of various types of HPMCAS dependent on pH and on the degree of neutralization of HPMCAS is discussed in detail in McGinity, James W. *Aqueous Polymeric Coatings for Pharmaceutical Dosage Forms*, New York: M. Dekker, 1989, pages 105-113. The above-mentioned article *Aqueous Polymeric Coatings for Pharmaceutical Dosage Forms* illustrates in FIG. 16 on p. 112 the dissolution time of several grades of HPMCAS, which have different degrees of substitution with succinoyl, acetyl and methoxyl groups, in pure water and in 0.1 N NaCl depending on the degree of neutralization of the HPMCAS. Depending on the HPMCAS and the presence or absence of NaCl, HPMCAS is soluble when it has a degree of neutralization between about 0.55 and 1. Below a degree of neutralization of about 0.55, all HPMCAS grades are insoluble in pure water and in 0.1 N NaCl.

Dosage forms coated with esterified cellulose ethers such as HPMCAS protect the drug from inactivation or degradation in the acidic environment of the stomach or prevent irritation of the stomach by the drug but release the drug in the small intestine. U.S. Pat. No. 4,365,060 discloses enterosoluble capsules. U.S. Pat. No. 4,226,981 discloses a process for preparing mixed esters of cellulose ethers, such as HPMCAS.

U.S. Pat. No. 4,365,060 discloses enterosoluble capsules which are said to have excellent enterosolubility behavior. The capsules are prepared from a mixed ester of an alkyl-, hydroxyalkyl- or hydroxyalkyl-alkyl-cellulose esterified with succinyl anhydride and an aliphatic monocarboxylic acid anhydride. The US patent discloses that the cellulose derivative can be shaped into capsules not only by the conventional dipping method but also by the plastic deformation at an elevated temperature under pressure such as compression molding, vacuum forming, matched-mold forming and the like. The US patent states that the enterosoluble capsules have excellent pliability. Unfortunately, the dipping method requires the use of an organic solvent for dissolving the mixed ester of an alkyl-, hydroxyalkyl- or hydroxyalkyl-alkyl-cellulose. Organic solutions of alkyl-, hydroxyalkyl- or hydroxyalkyl-alkyl-celluloses can also be used for coating dosage forms, such as tablets. However, organic solvents are often not desirable for pharmaceutical or nutritional uses. Moreover, the handling of organic solvents adds to the complexity of the process for producing the capsules and coatings. Forming capsules by plastic deformation is often not desirable either due to the significant thermal stress and thermal degradation caused by the heat that is needed for thermoforming or the complex and expensive molding process for thermoforming thin film capsules.

International Patent Application WO 2013/164121 teaches that many techniques for preparing capsules still require the combination of an enteric (acid insoluble) polymer and a conventional non-enteric polymer, require salts or pH regulators leading to water sensitivity or brittleness of the resulting capsule shells, require multiple processing steps, and/or need to be processed in non-aqueous media. To solve these problems, WO 2013/164121 discloses an aqueous composition comprising HPMCAS polymer dispersed in water, wherein the polymer is partially neutralized with at least one alkaline material, such as ammonia, sodium hydroxide, calcium hydroxide, potassium hydroxide, cationic polymers, and mixtures thereof. Unfortunately, the partial neutralization may impact the enteric properties of the capsules. E.g., stomach liquid may diffuse into the capsule upon ingestion when the capsule comprises partially neutralized HPMCAS.

Accordingly, there is still the urgent need to provide novel esterified cellulose ethers which are useful for coating dosage forms or for preparing polymeric capsule shells displaying enteric properties, particularly hard capsule shells. There is the particular need to provide coatings for dosage forms or polymeric capsule shells, which can be produced from aqueous solutions of esterified cellulose ethers but do not require the presence of pH regulators.

Surprisingly, a novel esterified cellulose ether has been found which is soluble in water, but which is resistant to dissolution in the acidic environment of the stomach. Surprisingly, the novel esterified cellulose ether also can be dissolved in organic solvents, such as acetone at a high concentration.

SUMMARY

One aspect of the present invention is an esterified cellulose ether which i) comprises groups of the formula —C(O)—R—COOH or a combination of aliphatic monovalent acyl groups and groups of the formula —C(O)—R—COOH, wherein R is a divalent hydrocarbon group, ii) has a weight average molecular weight $M_w$ of up to 70,000 Dalton, iii) has a degree of neutralization of the groups —C(O)—R—COOH of not more than 0.4, and iv) has a solubility in water of at least 2.0 weight percent at 2° C.

Another aspect of the present invention is a liquid composition which comprises at least one above-described esterified cellulose ether dissolved an aqueous diluent.

Yet another aspect of the present invention is a liquid composition which comprises at least one above-described esterified cellulose ether and an organic diluent.

Yet another aspect of the present invention is a process for coating a dosage form which comprises the step of contacting an above-mentioned liquid composition with the dosage form.

Yet another aspect of the present invention is a process for the manufacture of capsule shells which comprises the step of contacting the above-mentioned liquid composition with dipping pins.

Yet another aspect of the present invention is a coated dosage form wherein the coating comprises at least one above-described esterified cellulose ether.

Yet another aspect of the present invention is a polymeric capsule shell which comprises at least one above-described esterified cellulose ether.

Yet another aspect of the present invention is a capsule which comprises the above-mentioned capsule shell and further comprises a drug or a nutritional or food supplement or a combination thereof.

Yet another aspect of the present invention is a solid dispersion of at least one active ingredient in at least one above-described esterified cellulose ether.

DESCRIPTION OF EMBODIMENTS

Figure 1A:
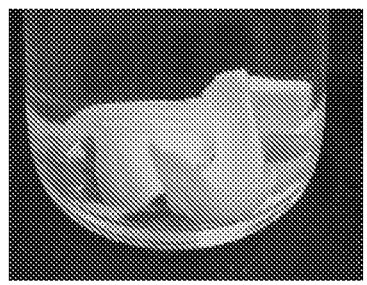
FIGS. 1A, 2A and 3A are photographical representations of non-dissolved pieces of capsule shells in 0.1 N HCl.

The esterified cellulose ether has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether of the present invention at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as an esterified hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.90, more preferably 0.12 to 0.70, most preferably 0.15 to 0.60, and particularly 0.20 to 0.40.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention preferably have a DS(alkoxyl) in the range of 1.0 to 2.5, more preferably from 1.1 to 2.4, most preferably from 1.2 to 2.2 and particularly from 1.6 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention comprises as ester groups groups of the formula —C(O)—R—COOH, wherein R is a divalent hydrocarbon group, such as —C(O)—CH$_2$—CH$_2$—COOH, and optionally aliphatic monovalent acyl groups, such as acetyl, propionyl, or butyryl, such as n-butyryl or i-butyryl. Specific examples of esterified cellulose ethers are hydroxypropyl methylcellulose acetate succinate (HPMCAS), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS), or methyl cellulose acetate succinate (MCAS). Hydroxypropyl methylcellulose acetate succinate (HPMCAS) is the most preferred esterified cellulose ether.

The esterified cellulose ether generally has a degree of substitution of groups of formula —C(O)—R—COOH, such as succinoyl, of at least 0.01, preferably at least 0.05, and most preferably at least 0.10. The esterified cellulose ethers generally have a degree of substitution of groups of formula —C(O)—R—COOH of up to 0.90, preferably up to 0.65, and more preferably up to 0.50. The esterified cellulose ethers generally have a degree of substitution of aliphatic monovalent acyl groups, such as acetyl, propionyl, or butyryl groups, of 0 or at least 0.05, preferably at least 0.10, and more preferably at least 0.25. The esterified cellulose ethers generally have a degree of substitution of aliphatic monovalent acyl groups of up to 0.95, preferably up to 0.80, and more preferably up to 0.60. The total degree of ester substitution is generally at least 0.05, preferably at least 0.10, and more preferably at least 0.20. The total degree of ester substitution is generally not more than 1.0, preferably not more than 0.90, and more preferably not more than 0.70.

The content of the acetate and succinate ester groups is determined according to "Hypromellose Acetate Succinate, United States Pharmacopia and National Formulary, NF 29, pp. 1548-1550". Reported values are corrected for volatiles (determined as described in section "loss on drying" in the above HPMCAS monograph). The method may be used in analogue manner to determine the content of propionyl, butyryl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) -$$
$$\left(\% \text{ HPO} * \frac{M(OCH_2CH(OH)CH_3) - M(OH)}{M(OCH_2CH(OH)CH_3)}\right) -$$
$$\left(\% \text{ Acetyl} * \frac{M(COCH_3) - M(H)}{M(COCH_3)}\right) -$$
$$\left(\% \text{ Succinoyl} * \frac{M(COC_2H_4COOH) - M(H)}{M(COC_2H_4COOH)}\right)$$

$$DS(Me) = \frac{\frac{\% MeO}{M(OCH_3)}}{\frac{\% \text{ cellulose backbone}}{M(AGU)}}$$

$$MS(HP) = \frac{\frac{\% HPO}{M(HPO)}}{\frac{\% \text{ cellulose backbone}}{M(AGU)}}$$

$$DS(\text{Acetyl}) = \frac{\frac{\% \text{ Acetyl}}{M(\text{Acetyl})}}{\frac{\% \text{ cellulose backbone}}{M(AGU)}}$$

$$DS(\text{Succinoyl}) = \frac{\frac{\% \text{ Succinoyl}}{M(\text{Succinoyl})}}{\frac{\% \text{ cellulose backbone}}{M(AGU)}}$$

$M(MeO) = M(OCH_3) = 31.03 \ Da$ $M(HPO) = M(OCH_2CH(OH)CH_3) = 75.09 \ Da$ $M(\text{Acetyl}) = M(COCH_3) = 43.04 \ Da$ $M(\text{Succinoyl}) = M(COC_2H_4COOH) = 101.08 \ Da$ $M(AGU) = 162.14 \ Da$ $M(OH) = 17.008 \ Da$ $M(H) = 1.008 \ Da$ By convention, the weight percent is an average weight percentage based on the total weight of the cellulose repeat unit, including all substituents. The content of the methoxyl group is reported based on the mass of the methoxyl group (i.e., —OCH$_3$). The content of the hydroxyalkoxyl group is reported based on the mass of the hydroxyalkoxyl group (i.e., —O— alkylene-OH); such as hydroxypropoxyl (i.e., —O—CH$_2$CH(CH$_3$)—OH). The content of the aliphatic monovalent acyl groups is reported based on the mass of —C(O)—R$_1$ wherein R$_1$ is a monovalent aliphatic group, such as acetyl (—C(O)—CH$_3$). The content of the group of formula —C(O)—R—COOH is reported based on the mass of this group, such as the mass of succinoyl groups (i.e., —C(O)—CH$_2$—CH$_2$—COOH).

The esterified cellulose ethers of the present invention have a weight average molecular weight $M_w$ of up to 70,000 Dalton, preferably up to 60,000 Dalton, and more preferably up to 50,000 Dalton or up to 40,000 Dalton. Generally they have a weight average molecular weight $M_w$ of at least 8,000 Dalton, preferably at least 10,000 Dalton, more preferably at least 12,000 Dalton, and most preferably at least 13,000 Dalton.

The water-soluble esterified cellulose ether generally has a polydispersity $M_w/M_n$, i.e., a ratio of weight average molecular weight $M_w$ to number average molecular weight $M_n$, of not more than 2.6, preferably not more than 2.1, more preferably not more than 2.0, most preferably not more than 1.8, and in some embodiments even not more than 1.5. The polydispersity $M_w/M_n$ generally is at least 1.1, typically at least 1.2 or at least 1.3. The surprisingly low polydispersity of the water-soluble esterified cellulose ether is highly desirable because a low polydispersity is an indication of a fairly tight molecular weight distribution. High tightness of molecular weight distribution is desirable for polymers that act as excipients in pharmaceutical dosage forms in order to increase reproducibility of the properties of individual dosage forms and to increase the uniformity of the interaction of the polymer molecules with the active ingredient, which maximizes the predictability of the efficiency of the dosage forms.

$M_w$ and $M_n$ are measured according to Journal of Pharmaceutical and Biomedical Analysis 56 (2011) 743 using a mixture of 40 parts by volume of acetonitrile and 60 parts by volume of aqueous buffer containing 50 mM NaH$_2$PO$_4$ and 0.1 M NaNO$_3$ as mobile phase. The mobile phase is adjusted to a pH of 8.0. The measurement of $M_w$ and $M_n$ is described in more details in the Examples.

In the esterified cellulose ether of the present invention the degree of neutralization of the groups —C(O)—R—COOH is not more than 0.4, preferably not more than 0.3, more preferably not more than 0.2, most preferably not more than 0.1, and particularly not more than 0.05 or even not more than 0.01. The degree of neutralization can even be essentially zero or only slightly above it, e.g. up to $10^{-3}$ or even only up to $10^{-4}$. The term "degree of neutralization" as used herein defines the ratio of deprotonated carboxylic groups over the sum of deprotonated and protonated carboxylic groups, i.e., Degree of neutralization=[—C(O)—R—COO$^-$]/[—C(O)—R—COO$^-$+—C(O)—R—COOH].

Another essential property of the esterified cellulose ether of the present invention is its water-solubility. Surprisingly, the esterified cellulose ether of the present invention has a solubility in water of at least 2.0 weight percent at 2° C., i.e., it can be dissolved as an at least 2.0 weight percent solution, preferably at least 3.0 weight percent solution, and more preferably at least 5.0 weight percent solution in water at 2° C. Generally the esterified cellulose ether of the present invention can be dissolved as up to 20 weight percent solution or in the most preferred embodiments even as up to 30 weight percent solution in water at a temperature of 2° C.

The term "an x weight percent solution in water at 2° C." as used herein means that x g of the esterified cellulose ether is soluble in (100–x) g of water at 2° C.

In more general terms, it has surprisingly been found that the esterified cellulose ether of the present invention comprising groups of the formula —C(O)—R—COOH is soluble in an aqueous liquid at a temperature of less than 10° C., more preferably less than 8° C., even more preferably less than 5° C., and most preferably up to 3° C., even when the esterified cellulose ether is blended with an aqueous liquid that does not increase the degree of neutralization of the esterified cellulose ether to more than 0.4 or a preferred range listed above, e.g., when the esterified cellulose ether is blended with only water, such as deionized or distilled water. This renders the esterified cellulose ether of the present invention very useful in a variety of application, e.g. for producing coatings and capsules. The aqueous liquid may additionally comprise a minor amount of an organic liquid diluent; however, the aqueous liquid should generally comprise at least 80, preferably at least 85, more preferably at least at least 90, and particularly at least 95 weight percent of water, based on the total weight of the aqueous liquid. The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. The aqueous liquid may comprise a basic compound, but the degree of neutralization of the groups —C(O)—R—COOH of the esterified cellulose ether in the resulting blend of esterified cellulose ether and aqueous liquid should not be more than 0.4, preferably not more than 0.3 or 0.2 or 0.1, more preferably not more than 0.05 or 0.01, and most preferably not more than $10^{-3}$ or even not more than $10^{-4}$. Preferably the aqueous liquid does not comprise a substantial amount of a basic compound. More preferably, the aqueous liquid does not contain a basic compound. Even more preferably, the aqueous liquid comprises from 80 to 100 percent, preferably 85 to 100 percent, more preferably 90 to 100 percent and most preferably 95 to 100 percent of water, and from 0 to 20 percent, preferably 0 to 15 percent, more preferably 0 to 10 percent, and most preferably 0 to 5 percent of an organic liquid diluent, based on the total weight of the aqueous liquid. Most preferably the aqueous liquid consists of water, e.g., deionized or distilled water.

When determining the water solubility as described in the Examples section, the esterified cellulose ether of the present invention preferably has solubility properties that at least 80 wt. %, typically at least 85 wt. %, more typically at least 90 wt. %, and in most cases at least 95 wt. %, of the esterified cellulose ether is soluble in a mixture of 2.5 weight parts of the esterified cellulose ether and 97.5 weight parts of water at 2° C. Typically this degree of solubility is also observed in a mixture of 5 or 10 weight parts of the esterified cellulose ether and 95 or 90 weight parts of water at 2° C. or even in a mixture of 20 weight parts of the esterified cellulose ether and 80 weight parts of water at 2° C.

The esterified cellulose ethers of the present invention generally have a viscosity of up to 100 mPa·s, preferably up to 50 mPa·s, and more preferably up to 5.0 mPa·s, measured as a 2.0 wt.-% solution of the esterified cellulose ether in 0.43 wt.-% aqueous NaOH at 20° C. Generally the viscosity is at least 1.2 mPa·s, more typically at least 1.8 mPa·s, even more typically at least 2.4 mPa·s, and most typically at least 2.8 mPa·s, measured as a 2.0 wt.-% solution of the esterified cellulose ether in 0.43 wt.-% aqueous NaOH at 20° C. The 2.0% by weight solution of the esterified cellulose ether is prepared as described in"Hypromellose Acetate Succinate, United States Pharmacopeia and National Formulary, NF 29, pp. 1548-1550", followed by an Ubbelohde viscosity measurement according to DIN 51562-1:1999-01 (January 1999).

Moreover, the esterified cellulose ethers of the present invention are soluble in acetone and have a surprisingly low viscosity, even at high concentrations. Generally the esterified cellulose ethers of the present invention have a viscosity of only up to 13 mPa·s, preferably up to 10 mPa·s, and more preferably up to 6 mPa·s, measured as a 10 wt.-% solution of the esterified cellulose ether in acetone at 20° C. The esterified cellulose ethers of the present invention typically have a viscosity of 2.0 mPa·s or more, more typically of 3.0 mPa·s or more, measured as a 10 wt.-% solution of the esterified cellulose ether in acetone at 20° C. Generally the esterified cellulose ethers of the present invention have a viscosity of only up to 40 mPa·s, more preferably only up to 30 mPa·s, and most preferably even only up 25 mPa·s to, measured as a 20 wt.-% solution of the esterified cellulose ether in acetone at 20° C. The esterified cellulose ethers of the present invention typically have a viscosity of 6 mPa·s or more, more typically of 10 mPa·s or more, measured as a 20 wt.-% solution of the esterified cellulose ether in acetone at 20° C. Esterified cellulose ethers having a very low viscosity in acetone are disclosed in International Patent Applications WO2014/137777 and WO2014/137778. However, the esterified cellulose ethers disclosed in these patent publications are not water soluble. Moreover, the esterified cellulose ethers that are disclosed in International Patent Applications WO2014/137777 and WO2014/137778 are produced from cellulose ethers of very low viscosity which have been subjected to very vigorous depolymerization processes which are cost-intensive and which may lead to discoloration of the cellulose ethers during depolymerization.

During extensive research the inventors of the present patent application have surprisingly found that a lower molecular portion of known esterified cellulose ethers comprising groups of the formula —C(O)—R—COOH is dissolved in an aqueous liquid when the esterified cellulose ether is blended with the aqueous liquid as defined above and the temperature of the resulting blend is set to a temperature of less than 10° C., preferably less than 8° C., more preferably less than 5° C., and particularly 3° C. or less. The higher molecular portion of the esterified cellulose ether remains un-dissolved, even at a temperature of less than 10° C. When the temperature of the blend has a temperature of 10° C. or more, such partial dissolution is not observed. Particularly at room temperature known esterified cellulose ethers comprising groups of the formula —C(O)—R—COOH do not dissolve in water to a noticeable degree.

Accordingly, the water soluble esterified cellulose ethers of the present invention can be produced in a process for fractionating an above-described esterified cellulose ether comprising groups of the formula —C(O)—R—COOH, which process comprises the steps of a) blending an esterified cellulose ether comprising groups of the formula —C(O)—R—COOH with an aqueous liquid as described above and setting the temperature of the resulting blend to less than 10° C. to dissolve a portion of the esterified cellulose ether in the aqueous liquid, b) separating the non-dissolved portion of the esterified cellulose ether from the remainder of the blend, and c) recovering the esterified cellulose ether that is dissolved in the aqueous liquid.

The temperature of the aqueous liquid used for preparing the blend in step a) preferably is 0° C. or more, typically 1° C. or more. The temperature of the aqueous liquid used in step a) is typically up to 20° C., preferably less than 10° C., more preferably less than 8° C., even more preferably less than 5° C., and most preferably up to 3° C. Generally the esterified cellulose ether is blended with at least 5 weight parts, preferably at least 10 weight parts, more preferably at least 20 weight parts, and generally up to 100 weight parts, preferably up to 60 weight parts, more preferably up to 40 weight parts, of aqueous liquid per weight part of esterified cellulose ether.

It is essential in the fractionation process that the temperature of the resulting blend in step a) is set to less than 10° C., preferably less than 8° C., more preferably less than 5° C., and most preferably to 3° C. or less. The temperature of the resulting blend is generally set to at least minus 2° C., typically to 0° C. or more, and more typically to 1° C. or more. It is not essential whether the temperature of the aqueous liquid is adjusted before or after blending with the esterified cellulose ether. Preferably the blend is left at the above-mentioned temperature for a time period of up to a week, more preferably up to 72 hours, and more preferably up to 24 hours. Preferably the blend is left at the above-mentioned temperature for a time period of at least 10 minutes, preferably at least 30 minutes, and more preferably at least 2 hours.

In step b) of the fractionation process the non-dissolved portion of the esterified cellulose ether can be separated from the remainder of the blend in a known manner, such as by centrifugation or filtration or upon settling by decantation. It can be used for known purposes. After separation of the esterified cellulose ether from the remainder of the blend at a temperature of less than 10° C. as described above, the remainder of the blend surprisingly still comprises dissolved esterified cellulose ether. The portion of the dissolved esterified cellulose ether is generally at least 1 percent, typically at least 5 percent, and generally up to 70 percent, typically up to 50 percent, based on the total weight of the esterified cellulose ether. The dissolved esterified cellulose ether is invisible to the naked eye.

In step c) of the fractionation process the esterified cellulose ether that is dissolved in the aqueous liquid is recovered e.g., by heating the aqueous liquid comprising the dissolved esterified cellulose ether to a temperature of at least 30° C., preferably at least 45° C. more preferably at least 60° C., and most preferably at least 80° C. Typically the aqueous liquid comprising the dissolved esterified cellulose ether is heated to a temperature of up to 98° C., more typically of up to 95° C. At such temperatures the dissolved esterified cellulose ether precipitates. The precipitated esterified cellulose ether can be separated from the aqueous liquid in a known manner, such as by centrifugation or filtration or upon settling by decantation. The observed water-insolubility of this esterified cellulose ether upon heating is reversible. The separated esterified cellulose ether is soluble in an aqueous liquid at a temperature of less than 10° C. Alternatively, the esterified cellulose ether that is dissolved in the aqueous liquid is recovered in step c) of the fractionation process by freeze-drying.

The above-described method of recovering water soluble esterified cellulose ethers of the present invention can be integrated in a process for producing esterified cellulose ethers from cellulose ethers. Hence, one process comprises the steps of a) reacting a cellulose ether with a dicarboxylic acid anhydride or with a combination of a dicarboxylic acid anhydride and an aliphatic monocarboxylic acid anhydride in the presence of an aliphatic carboxylic acid to produce a reaction product mixture comprising an esterified cellulose ether comprising groups of the formula —C(O)—R—COOH, precipitating the esterified cellulose ether from the reaction product mixture, blending the precipitated esterified cellulose ether with an aqueous liquid and setting the temperature of the resulting blend to less than 10° C. to dissolve a portion of the esterified cellulose ether in the aqueous liquid, b) separating the non-dissolved portion of the esterified cellulose ether from the remainder of the blend, and c) recovering the esterified cellulose ether that is dissolved in the aqueous liquid.

The reaction of a cellulose ether with a dicarboxylic acid anhydride or with a combination of a dicarboxylic acid anhydride and an aliphatic monocarboxylic acid anhydride in the presence of an aliphatic carboxylic acid to produce a reaction product mixture comprising an esterified cellulose ether can be conducted in a known manner, for example as described in U.S. Pat. Nos. 3,435,027 and 4,226,981, in the International Patent Applications WO 2005/115330 or WO2013/148154, or in European Patent Application EP 0 219 426.

The resulting reaction product mixture comprises the esterified cellulose ether, typically an aliphatic carboxylic acid used as a reaction medium, typically a reaction catalyst, such as an alkali metal carboxylate, typically residual amounts of one or more esterification agents and by-products, such as a dicarboxylic acid anhydride and optionally an aliphatic monocarboxylic acid anhydride. The reaction product mixture generally comprises from 3 to 60 weight percent, typically from 7 to 35 weight percent of the esterified cellulose ether, generally from 10 to 95 weight percent, typically from 20 to 70 weight percent of the aliphatic carboxylic acid, generally from 1 to 50 weight percent, typically from 5 to 30 weight percent, of a reaction catalyst, such as an alkali metal carboxylate, and generally from 0.1 to 50, typically from 2 to 40 weight percent of minor components, such as a non-reacted dicarboxylic acid anhydride and optionally a non-reacted aliphatic monocarboxylic acid anhydride, all percentages being based on the total weight of the reaction product mixture. The reaction product mixture comprising the esterified cellulose ether generally has a temperature of 60° C. or more, typically of 75° C. or more, and generally up to 110° C., typically up to 90° C.

After completion of the esterification reaction, the esterified cellulose ether is precipitated from the resulting reaction product mixture. The esterified cellulose ether can be precipitated from the reaction mixture in a known manner, for example as described in U.S. Pat. No. 4,226,981, International Patent Application WO 2005/115330, European Patent Application EP 0 219 426 or International Patent Application WO2013/148154.

The precipitated esterified cellulose ether is subsequently washed with an aqueous liquid. Suitable aqueous liquids are described further above. In the washing step the precipitated esterified cellulose ether is blended with an aqueous liquid; preferably 2 to 400 weight parts, more preferably 3 to 300 weight parts, and most preferably 4 to 150 weight parts of aqueous liquid are used per weight part of esterified cellulose ether. The washing step can be repeated once or several times, preferably once to 5 times. Surprisingly, it has been found that a portion of the precipitated esterified cellulose ether is dissolved in the aqueous liquid used for washing purposes when the blend of esterified cellulose ether and aqueous liquid is set to a temperature of less than 10° C., preferably to less than 8° C., more preferably to less than 5° C., and most preferably to 3° C. or less.

In step b) of the production process the non-dissolved portion of the esterified cellulose ether, i.e., the portion of the esterified cellulose ether that does not dissolve in the blend of esterified cellulose ether and aqueous liquid at a temperature of less than 10° C., can be separated from the remainder of the blend as described above in step b) of the fractionation process.

In step c) of the production process the esterified cellulose ether that is dissolved in the aqueous liquid is recovered as described above in step c) of the fractionation process. The esterified cellulose ether of the present invention having the properties as described further above is obtained in step c) of the production process Another aspect of the present invention is a liquid composition comprising one or more of the above described esterified cellulose ethers of the present invention dissolved in an aqueous diluent. The term "liquid composition" as used herein means a composition that is liquid at 25° C. and atmospheric pressure. The aqueous diluent preferably is water alone or water mixed with a minor amount of an organic liquid diluent as described above. In this embodiment the composition of the present invention comprises more than 50, preferably at least 65, more preferably at least 80, most preferably at least at least 90, and particularly at least 95 weight percent of water and less than 50, preferably up to 35, more preferably up to 20, most preferably up to 10, and particularly up to 5 weight percent of an organic liquid diluent, based on the total weight of the organic liquid diluent and water. The aqueous diluent may comprise a basic compound, but the degree of neutralization of the groups —C(O)—R—COOH of the esterified cellulose ether in the resulting blend of esterified cellulose ether and aqueous liquid should not be more than 0.4, preferably not more than 0.3 or 0.2 or 0.1, more preferably not more than 0.05 or 0.01, and most preferably not more than $10^{-3}$ or even not more than $10^{-4}$. Preferably the aqueous diluent does not comprise a substantial amount of a basic compound. More preferably, the aqueous diluent does not contain a basic compound. The liquid composition preferably comprises at least 5 wt.-%, more preferably at least 10 wt.-%, and even more preferably at least 15 wt.-% of the esterified cellulose ether of the present invention, based on the total weight of the liquid composition. The liquid composition generally comprises up to 20 wt.-% or in preferred embodiments even up to 30 wt.-% of the esterified cellulose ether of the present invention, based on the total weight of the liquid composition. The esterified cellulose ether of the present invention can be brought into solution by cooling the liquid composition to a temperature of −2° C. to less than 10° C., preferably of 0° C. to less than 8° C., more preferably of 0.5° C. to less than 5° C., and most preferably of 0.5° C. to 3° C.

The liquid composition comprising an aqueous diluent and one or more of the above described esterified cellulose ethers is particularly useful in the manufacture of capsules which comprises the step of contacting the liquid composition with dipping pins. Partial neutralization of the esterified cellulose ether, which might impact the enteric properties of the esterified cellulose ether, is not needed. Furthermore, the capsules can even be prepared at about room temperature, which results in savings in energy. Typically the liquid aqueous composition having a temperature of less than 10° C. is contacted with dipping pins that have a temperature of at least 15° C., preferably at least 20° C., more preferably at least 30° C. and up to 95° C., preferably up to 70° C., and more preferably up to 60° C. The capsules have enteric properties.

The liquid composition comprising an aqueous diluent and one or more of the above described esterified cellulose ethers dissolved therein is also useful for coating dosage forms, such as tablets, granules, pellets, caplets, lozenges, suppositories, pessaries or implantable dosage forms.

Another aspect of the present invention is a liquid composition comprising an organic diluent and one or more of the above described esterified cellulose ethers of the present invention. The organic diluent may be present in the liquid composition alone or mixed with water. In this embodiment the composition of the present invention preferably comprises at least 50, more preferably at least 65, most preferably at least 75, and particularly at least 90 weight percent of an organic liquid diluent and preferably up to 50, more preferably up to 35, most preferably up to 25, and particularly up to 10 weight percent of water, based on the total weight of the organic liquid diluent and water. Most preferably the liquid composition comprising an organic diluent and one or more of the above described esterified cellulose ethers of the present invention does not comprise a substantial amount of water. Preferred organic diluents are described further above. The esterified of the present invention is soluble in organic liquid diluents, such as acetone, at high concentrations at 20° C. The solutions have a low viscosity, even at high concentrations, e.g. at 10 to 20 weight percent or even higher. The liquid composition preferably comprises at least 5 wt.-%, more preferably at least 10 wt.-%, and even more preferably at least 15 wt.-% of the esterified cellulose ether of the present invention, based on the total weight of the liquid composition. The liquid composition generally comprises up to 20 wt.-% or in preferred embodiments even up to 30 wt.-% of the esterified cellulose ether of the present invention, based on the total weight of the liquid composition. This embodiment of the invention is particularly useful if the present invention comprises an active ingredient of poor water solubility.

The composition of the present invention comprising a liquid diluent and one or more of the above described esterified cellulose ethers is also useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. The liquid composition of the present invention preferably comprises from 1 to 40 percent, more preferably from 5 to 35 percent, even more preferably from 7 to 30 percent, most preferably from 10 to 25 percent of at least one esterified cellulose ether as described above and from 40 to 99 percent, more preferably from 50 to 94.9 percent, even more preferably from 65 to 92.5 percent and most preferably from 70 to 89 percent of a liquid diluent described further above. Furthermore, the liquid composition of the present invention generally comprises from 0 to 40 percent, more preferably from 0.1 to 40 percent, even more preferably from 0.5 to 25 percent, and most preferably from 1 to 15 percent of an active ingredient, based on the total weight of the composition. The low viscosity of the esterified cellulose ether, measured as a 10 wt. % or even 20 wt. % solution in acetone at 20° C., and the high solubility of the esterified cellulose ether in water at a temperature of less than 10° C. allows the incorporation of a high concentration of the esterified cellulose ether, i.e., a high ratio of esterified cellulose ether to liquid diluent, while still providing a liquid composition of reasonably low viscosity. This can be utilized in two ways to produce solid dispersions of an active ingredient in an esterified cellulose ether: 1. Either the ratio of esterified cellulose ether/active ingredient is kept the same as in known, more dilute compositions. In this case a higher concentration of the esterified cellulose ether also leads to a higher concentration of the active ingredient in the liquid composition, and, accordingly to an increased throughput of the active ingredient in the production of solid dispersions while maintaining the same stability of the active ingredient. 2. Alternatively, only the concentration of the esterified cellulose ether in the liquid composition is increased, but not the concentration of the active ingredient. This leads to a higher ratio of esterified cellulose ether/active ingredient, which leads to an improved stabilization of the active ingredient in the matrix of the esterified cellulose ether upon removal of the liquid diluent without decreasing the throughput of the active ingredient. This means that formulators can operate at a higher content of the esterified cellulose ether in the liquid formulation—without the need to reduce the content of the active ingredient—in order to achieve enhanced stabilization of the amorphous state of an active ingredient in a solid dosage form. The esterified cellulose ethers of the present invention allow a high loading of the active ingredient in the liquid composition while still achieving a reasonably high throughput in preparing a solid dispersion.

In another aspect of the invention the liquid composition of the present invention is used for producing a solid dispersion comprising at least one active ingredient, such as a drug, at least one esterified cellulose ether as described above and optionally one or more adjuvants. The solid dispersion is produced by removing the liquid diluent from the composition. The low viscosity of the esterified cellulose ether in acetone or another organic solvent allows the incorporation of a high concentration of the esterified cellulose ether, and accordingly a high concentration of a drug, into the composition while still maintaining a reasonably low viscosity of the liquid composition. This is highly advantageous for achieving a high throughput when the liquid composition is used for coating purposes or when the comprising the esterified cellulose ether is subjected to spray-drying, for example for preparing solid dispersions comprising an active ingredient and an esterified cellulose ether. Moreover, liquid formulations using a high ratio of esterified cellulose ether to active ingredient, as described above, can be formulated with spray drying. A high ratio of esterified cellulose ether to active ingredient is desired in maintaining supersaturation of poorly soluble active ingredients and for increasing its bioavailability.

A preferred method of producing a solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7-page 35, line 25. Alternatively, the solid dispersion of the present invention may be prepared by i) blending a) at least one esterified cellulose ether defined above, b) one or more active ingredients and c) one or more optional additives, and ii) subjecting the blend to extrusion. The term "extrusion" as used herein includes processes known as injection molding, melt casting and compression molding. Techniques for extruding, preferably melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The solid dispersion of the present invention preferably comprises a) from 20 to 99.9 percent, more preferably from 30 to 98 percent, and most preferably from 60 to 95 percent of an esterified cellulose ether as described above, and b) preferably from 0.1 to 80 percent, more preferably from 2 to 70 percent, and most preferably from 5 to 40 percent of an active ingredient, based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, consists of c) one or more of the adjuvants as described below. The solid dispersion can comprise one or more of the esterified cellulose ethers a), one or more of the active ingredients b), and optionally one or more of the adjuvants c), however their total amount is generally within the above-mentioned ranges. Once the solid dispersion comprising at least one active ingredient in at least one esterified cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms. The solid dispersion of the present invention may be in various forms, such as in the form of strands, pellets, granules, pills, tablets, caplets, microparticles, fillings of capsules or injection molded capsules or in the form of a powder, film, paste, cream, suspension or slurry.

The liquid composition and the solid dispersion of the present invention may further comprise optional additives, such as coloring agents, pigments, opacifiers, flavor and taste improvers, antioxidants, and any combination thereof. Optional additives are preferably pharmaceutically acceptable. Useful amounts and types of one or more optional adjuvants are generally known in the art and depend on the intended end-use of the liquid composition or the solid dispersion of the present invention.

Some embodiments of the invention will now be described in detail in the following Examples.

EXAMPLES

Unless otherwise mentioned, all parts and percentages are by weight. In the Examples the following test procedures are used.

Content of Ether and Ester Groups

The content of ether groups in the esterified cellulose ether is determined in the same manner as described for "Hypromellose", United States Pharmacopeia and National Formulary, USP 35, pp 3467-3469.

The ester substitution with acetyl groups (—CO—CH$_3$) and the ester substitution with succinoyl groups (—CO—CH$_2$—CH$_2$—COOH) are determined according to Hypromellose Acetate Succinate, United States Pharmacopia and National Formulary, NF 29, pp. 1548-1550". Reported values for ester substitution are corrected for volatiles (determined as described in section "loss on drying" in the above HPMCAS monograph).

Water-Solubility

Qualitative Determination:

A 2 wt. percent mixture of HPMCAS and water was prepared by mixing 2.0 g HPMCAS, based on its dry weight, with 98.0 g water under vigorous stirring at 0.5° C. for 16 hours. The temperature of the mixture of HPMCAS and water was then increased to 5° C. The water solubility of the esterified cellulose ether was determined by visual inspection. The determination whether the HPMCAS was water-soluble at 2% at 5° C. or not was done as follows. "Water soluble at 2%—yes" means that a solution without sediment was obtained according to the procedure above. "Water soluble at 2%—no" means that at least a significant portion of the HPMCAS remained undissolved and formed sediment when mixing 2.0 g HPMCAS, based on its dry weight, with 98.0 g water according to the procedure above. "Water soluble at 2%—partially" means that only a small portion of the HPMCAS remained undissolved and formed sediment when mixing 2.0 g HPMCAS, based on its dry weight, with 98.0 g water according to the procedure above.

Quantitative Determination:

2.5 weight parts of HPMCAS, based on its dry weight, were added to 97.5 weight parts of deionized water having a temperature of 2° C. followed by stirring for 6 hours at 2° C. and storing for 16 h at 2° C. A weighed amount of this mixture was transferred to a weighed centrifuge vial; the transferred weight of the mixture was noted as M1 in g. The transferred weight of HPMCAS [M2] was calculated as (transferred weight of mixture in g/100 g*2.5 g). The mixture was centrifuged for 60 min at 5000 rpm (2823 xg, Biofuge Stratos centrifuge from Thermo Scientific) at 2° C. After centrifugation an aliquot was removed from the liquid phase and transferred to a dried weighed vial. The weight of the transferred aliquot was recorded as M3 in g. The aliquot was dried at 105° C. for 12 h. The remaining g of HPMCAS was weighted after drying and recorded as M4 in g.

The term "% water soluble at 2.5%" in Table 2 below expresses the percentage of HPMCAS that is actually dissolved in the mixture of 2.5 weight parts of HPMCAS and 97.5 weight parts of deionized water. It is calculated as (M4/M2)*(M1/M3)*100), which corresponds to (g HPMCAS in liquid aliquot/g HPMCAS transferred to centrifuge vial)*(g mixture transferred to centrifuge vial/g liquid aliquot after centrifugation).

Viscosity of Hydroxypropyl Methyl Cellulose Acetate Succinate (HPMCAS)

The 2.0% by weight solution of the HPMCAS in 0.43 wt. % aqueous NaOH was prepared as described in"Hypromellose Acetate Succinate, United States Pharmacopia and National Formulary, NF 29, pp. 1548-1550", followed by an Ubbelohde viscosity measurement at 20° C. according to DIN 51562-1:1999-01 (January 1999).

The 10 wt.-% solution of HPMCAS in acetone was prepared by mixing 10.0 g HPMCAS, based on its dry weight, with 90.0 g of acetone under vigorous stirring at room temperature. The mixture was rolled on a roller mixer for about 24 hours. The solution was centrifuged at 2000 rpm for 3 minutes using a Megafuge 1.0 centrifuge, commercially available from Heraeus Holding GmbH, Germany. An Ubbelohde viscosity measurement according to DIN 51562-1:1999-01 (January 1999) was carried out. The measurement was done at 20° C.

The 20 wt.-% solution of HPMCAS in acetone was prepared by mixing 20.0 g HPMCAS, based on its dry weight, with 80.0 g of acetone under vigorous stirring at room temperature. The mixture was rolled on a roller mixer for about 24 hours. The solution was centrifuged at 2000 rpm for 3 minutes using a Megafuge 1.0 centrifuge, commercially available from Heraeus Holding GmbH, Germany. An Ubbelohde viscosity measurement according to DIN 51562-1:1999-01 (January 1999) was carried out. The measurement was done at 20° C.

Determination of $M_w$ and $M_n$

Mw and Mn are measured according to Journal of Pharmaceutical and Biomedical Analysis 56 (2011) 743-747 unless stated otherwise. The mobile phase was prepared by mixing a mixture of 40 parts by volume of acetonitrile and 60 parts by volume of aqueous buffer containing 50 mM $NaH_2PO_4$ and 0.1 M $NaNO_3$. The mobile phase was adjusted to a pH of 8.0. Solutions of the cellulose ether esters were filtered into a HPLC vial through a syringe filter of 0.45 µm pore size.

More specifically, the utilized Chemicals and solvents were:

Polyethylene oxide standard materials (abbreviated as PEOX 20 K and PEOX 30 K) were purchased from Agilent Technologies, Inc. Palo Alto, Calif., catalog number PL2083-1005 and PL2083-2005.

Acetonitrile (HPLC grade ≥99.9%, CHROMASOL plus), catalog number 34998, sodium hydroxide (semiconductor grade, 99.99%, trace metal base), catalog number 306576, water (HPLC grade, CHROMASOLV Plus) catalog number 34877 and sodium nitrate (99,995%, trace metal base) catalog number 229938 were purchased from Sigma-Aldrich, Switzerland.

Sodium dihydrogen phosphate (≥99.999% TraceSelect) catalog number 71492, was purchased from FLUKA, Switzerland.

The normalization solution of PEOX20 K at 5 mg/mL, the standard solution of PEOX30 K at 2 mg/mL, and the sample solution of HPMCAS at 2 mg/mL were prepared by adding a weighed amount of polymer into a vial and dissolving it with a measured volume of mobile phase. All solutions were allowed to dissolve at room temperature in the capped vial for 24 h with stirring using a PTFE-coated magnetic stirring bar.

The normalization solution (PEOX 20k, single preparation, N) and the standard solution (PEOX30 K, double preparation, S1 and S2) were filtered into a HPLC vial through a syringe filter of 0.02 µm pore size and 25 mm diameter (Whatman Anatop 25, catalog number 6809-2002), Whatman.

The test sample solution (HPMCAS, prepared in duplicate, T1, T2) and a laboratory standard (HPMCAS, single preparation, LS) were filtered into a HPLC vial through a syringe filter of 0.45 µm pore size (Nylon, e.g. Acrodisc 13 mm VWR catalog number 514-4010).

Chromatographic condition and run sequence were conducted as described by Chen, R. et al.; Journal of Pharmaceutical and Biomedical Analysis 56 (2011) 743-748). The SEC-MALLS instrument set-up included a HP1100 HPLC system from Agilent Technologies, Inc. Palo Alto, Calif.; a DAWN Heleos II 18 angle laser light scattering detector and a OPTILAB rex refractive index detector, both from Wyatt Technologies, Inc. Santa Barbara, Calif. The analytical size exclusion column (TSK-GEL® GMPWXL, 300×7.8 mm) was purchased from Tosoh Bioscience. Both the OPTILAB and the DAWN were operated at 35° C. The analytical SEC column was operated at room temperature (24±5° C.). The mobile phase was a mixture of 40 volume parts of acetonitrile and 60 volume parts of aqueous buffer containing 50 mM NaH2PO4 and 0.1 M NaNO3 prepared as follows:

Aqueous buffer: 7.20 g of sodium dihydrogen phosphate and 10.2 g of sodium nitrate were added to 1.2 L purified water in a clean 2 L glass bottle under stirring until dissolution.

Mobile phase: 800 mL of acetonitrile were added to 1.2 L of the aqueous buffer prepared above, and stirred until a good mixture was achieved and the temperature equilibrated to ambient temperature.

The mobile phase was pH adjusted to 8.0 with 10M NaOH and filtered through a 0.2 m nylon membrane filter. The flow rate was 0.5 mL/min with in-line degassing. The injection volume was 100 μL and the analysis time was 35 min.

The MALLS data were collected and processed by Wyatt ASTRA software (version 5.3.4.20) using dn/dc value (refractive index increment) of 0.120 mL/g for HPMCAS. The light scattering signals of detector Nos. 1-4, 17, and 18) were not used in the molecular weight calculation. A representative chromatographic run sequence is given below: B, N, LS, S1 (5×), S2, T1 (2×), T2 (2×), T3 (2×), T4 (2×), S2, T5(2×), etc., S2, LS, W, where, B represents blank injection of mobile phase, N1 represents normalization solution; LS represents a laboratory standard HPMCAS; S1 and S2 represent standard solutions one and two, respectively; T1, T2, T3, T4, and T5 represent test sample solutions and W represents water injection. (2×) and (5×) denote the number of injections of the same solution.

Both the OPTILAB and the DAWN were calibrated periodically according to the manufacturer's recommended procedures and frequency. A 100 μL injection of a 5 mg/mL polyethylene oxide standard (PEOX20 K) was employed for normalizing all angle light scattering detectors relative to 90° detector for each run sequence.

Use of this mono-dispersed polymer standard also enabled the volume delay between the OPTILAB and the DAWN to be determined, permitting proper alignment of the light scattering signals to the refractive index signal. This is necessary for the calculation of the weight-averaged molecular weight (Mw) for each data slice.

Example 1: Preparation of Water Soluble HPMCAS

A hydroxypropyl methyl cellulose acetate succinate (HP-MCAS) having the properties listed in Table 1 below was used as a starting material for producing the water-soluble HPMCAS of the present invention. 750 g of the HPMCAS having a temperature of 20° C. was suspended in 4.6 liter of water having a temperature of 2° C. under stirring for 2 h and stored for 12 h at 3° C. The resulting blend of HPMCAS and water had a temperature of 3° C. A portion of the HPMCAS was dissolved in the blend at the temperature of 3° C. Then the liquid portion of the blend was separated from the suspended HPMCAS by centrifugation (Microfuge 1.0, Heraeus, 10000 rpm, 20 min) at a temperature of 1° C.

The properties of the HPMCAS starting material and of the obtained water soluble HPMCAS are listed in Table 1 below. In addition to the properties listed in Table 1 below, the viscosity of a 20 wt.-% solution of the water-soluble HPMCAS in acetone was determined. It was 22.8 mPa·s.

HPMCAS of Comparative Examples CE-11 to CE-16, CE-D and CE-E, as Described in WO 2014/137777

Comparative Examples CE-11 to CE-16 and Comparative Examples CE-D and CE-E correspond to Examples 11-16 and Comparative Examples D and E of the International Patent Application No. WO 2014/137777. Their production is described in detail in the International Patent Application WO 2014/137777 on pages 22 and 23.

HPMCAS of Comparative Example CE-C, as Described in WO/2014/031422

Comparative Example CE-C corresponds to Comparative Example C of the International Patent Application WO/2014/031422. Its production is described in detail in the International Patent Application WO/2014/031422 on page 25.

Comparative Examples CE-H to CE-J

Comparative Examples CE-H to CE-J correspond to Comparative Examples H to J of the International Patent Application No. WO 2014/137777. As disclosed in WO 2014/137777 on page 24 and in International Patent Application WO 2011/159626 on pages 1 and 2, HPMCAS is currently commercially available from Shin-Etsu Chemical Co., Ltd. (Tokyo, Japan), known by the trade name "AQOAT". Shin-Etsu manufactures three grades of AQOAT polymers that have different combinations of substituent levels to provide enteric protection at various pH levels, AS-L, AS-M, and AS-H, typically followed by the designation "F" for fine or "G", such as AS-LF or AS-LG. Their sales specifications are listed in Table 1 on page 2 of WO 2011/159626 and in WO 2014/137777 on page 24. According to the Technical Brochure of Shin-Etsu "Shin-Etsu AQOAT Enteric Coating Agent" edition 04.9 05.2/500, all grades of AQOAT polymers are soluble in 10% NaOH but insoluble in purified water. The data of analyzed samples of all grades of AQOAT polymers are disclosed in Table 2 on page 13 of WO 2011/159626.

The properties of the HPMCAS of Comparative Examples CE-11 to CE-16, CE-C, CE-D, CE-E and CE-H to CE-J are listed in Table 1 below. The abbreviation "n.a." means "not assessed".

TABLE 1

| | Molecular weight (kDA) | | | 10% viscosity in acetone [mPa · s] | 2% viscosity in NaOH [mPa · s] | Ether Substitution | | Ether substitution Acetyl (%) |
|---|---|---|---|---|---|---|---|---|
| HPMCAS | $M_n$ | $M_w$ | $M_w/M_n$ | | | Methoxyl (%) | Hydroxypropoxyl (%) | |
| Starting material in Example 1 | 46 | 114 | 2.5 | 18 | 2.85 | 22.8 | 7.2 | 8.0 |

TABLE 1-continued

| HPMCAS | Water soluble HPMCAS of Example 1 | | | | | | | |
|---|---|---|---|---|---|---|---|---|
| | 11.1 | 13.6 | 1.2 | 3.3 | 1.79 | 25.6 | 6.8 | 7.1 |
| CE-11 | 11 | 24 | 2.2 | 1.97 | 1.60 | 23.1 | 7.8 | 10.0 |
| CE-12 | 10 | 41 | 4.1 | 1.81 | 1.49 | 22.7 | 7.7 | 9.8 |
| CE-13 | 12 | 112 | 9.3 | 2.41 | 1.49 | 22.7 | 7.7 | 10.2 |
| CE-14 | 16 | 68 | 4.3 | 7.9 | 2.0 | 23.4 | 7.8 | 9.1 |
| CE-15 | 20 | 105 | 5.3 | 8.5 | 2.0 | 23.3 | 7.8 | 9.4 |
| CE-16 | 28 | 158 | 5.6 | 10.4 | 2.0 | 23.1 | 7.9 | 9.3 |
| CE-C | 23 | 53 | 2.3 | n.a. | 2.90 | 23.7 | 7.6 | 5.8 |
| CE-D | 36 | 139 | 3.9 | 37.4 | 2.61 | 22.7 | 7.5 | 11.0 |
| CE-E | 26 | 65 | 2.5 | 16.6 | 2.89 | 22.9 | 7.3 | 5.7 |
| CE-H | 33 | 153 | 4.6 | 27.7 | 3.0 | 22.5 | 7.0 | 8.1 |
| CE-I | 27 | 114 | 4.2 | 26.5 | 2.94 | 23.1 | 7.3 | 9.3 |
| CE-J | 29 | 137 | 4.7 | 29.8 | 2.89 | 23.6 | 7.2 | 11.6 |

| HPMCAS | Ester substitution Succinoyl (%) | Ether Substitution | | Ester substitution | | % water soluble at 2.5% | Water-soluble at 2% |
|---|---|---|---|---|---|---|---|
| | | $DS_M$ | $MS_{HP}$ | $DOS_{Ac}$ | $DOS_s$ | | |
| Starting material in Example 1 | 14.5 | 1.92 | 0.25 | 0.49 | 0.38 | n.m. | no |
| Water soluble HPMCAS of Example 1 | 11.2 | 2.05 | 0.23 | 0.41 | 0.28 | 100 | yes |
| CE-11 | 11.3 | 1.93 | 0.27 | 0.60 | 0.29 | 71 | no |
| CE-12 | 12.3 | 1.91 | 0.27 | 0.59 | 0.32 | 50 | no |
| CE-13 | 11.6 | 1.90 | 0.27 | 0.62 | 0.30 | 51 | no |
| CE-14 | 11.5 | 1.94 | 0.27 | 0.54 | 0.29 | 62 | no |
| CE-15 | 11.7 | 1.94 | 0.27 | 0.56 | 0.30 | 51 | no |
| CE-16 | 11.4 | 1.91 | 0.27 | 0.56 | 0.29 | 43 | no |
| CE-C | 14.7 | 1.96 | 0.26 | 0.35 | 0.37 | 67 | no |
| CE-D | 12.1 | 1.94 | 0.26 | 0.68 | 0.32 | 11 | no |
| CE-E | 16.0 | 1.91 | 0.25 | 0.34 | 0.41 | 51 | no |
| CE-H | 14.7 | 1.90 | 0.24 | 0.49 | 0.38 | 12 | no |
| CE-I | 10.6 | 1.88 | 0.24 | 0.54 | 0.26 | 45 | no |
| CE-J | 7.9 | 1.90 | 0.24 | 0.67 | 0.19 | 31 | no | n.m.: not measured

Example 2: Preparation of Capsules from Water Soluble HPMCAS

An aqueous solution of 25 wt.-% of the water soluble HPMCAS obtained according to the procedure in Example 1 was prepared by dissolving the HPMCAS in deionized water at a temperature of 2° C.

Capsule shells were produced by dipping metallic pins having a temperature of 21° C., 30° C. and 55° C., respectively, into the HPMCAS solution having a temperature of 5° C. The pins were then withdrawn from the aqueous HPMCAS solution and a film was formed on the molding pins. Capsule shells formed on the pins at each of these temperatures. The capsule shells formed on pins having room temperature (21° C.) were dried at room temperature, the capsule shells formed on pins having a temperature of 30° C. were dried at 30° C. and the capsule shells formed on pins having a temperature of 55° C. were dried at 55° C.

Figure 1B:
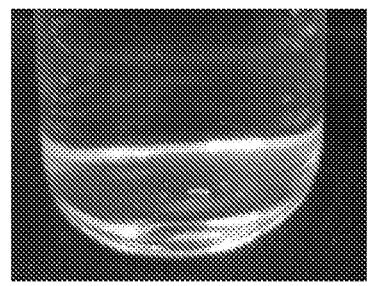
FIGS. 1B, 2B and 3B are photographical representations of aqueous buffer solutions of pH 6.8 into which the non-dissolved pieces of capsule shells shown in FIGS. 1A, 2A and 3A have been placed; all pieces of capsule shells are dissolved in the aqueous buffer solutions of pH 6.8.
Figure 2A:
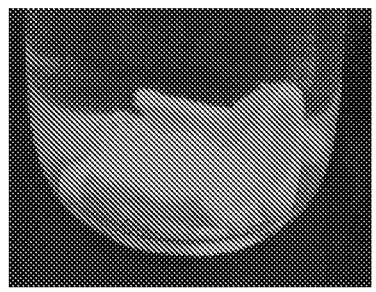
Figure 3A:
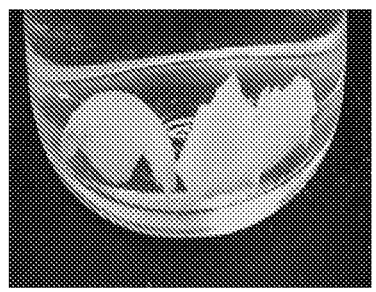

To test the solubility of the capsule shells in the acidic environment of the stomach, the capsule shells were broken into pieces and immersed into 0.1 N HCl. The capsule pieces were left there for 12 h at a temperature of 21° C. The capsule pieces did not dissolve in 0.1 N HCl during these 12 hours. The capsule pieces could be seen by the unprotected eye in 0.1 N HCl during these entire 12 hours. FIGS. 1A, 2A and 3A show the non-dissolved pieces of capsule shells in 0.1 N HCl. FIG. 1A illustrates pieces of capsule shells prepared on pins having room temperature, FIG. 1B illustrates pieces of capsule shells prepared on pins having a temperature of 30° C. and FIG. 1C illustrates pieces of capsule shells prepared on pins having a temperature of 55° C.

Figure 2B:
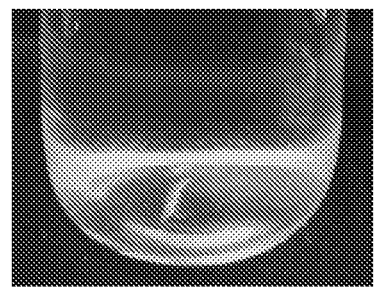
Figure 3B:
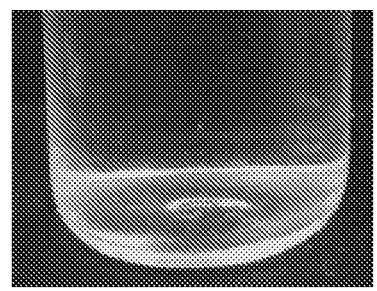

To test the solubility of the capsule shells in a neutral environment, the 0.1 N HCl was poured off from the capsule pieces and the capsule pieces were put into a McIlvaine's buffer solution (containing disodium monophosphate and citric acid) having a pH of 6.8. After about 60 minutes all pieces of capsule shells were completely dissolved in the buffer of pH 6.8 leaving clear solutions. FIGS. 1B, 2B and 3B are photographical representations of the McIlvaine's buffer solution of pH 6.8 into which the non-dissolved pieces of capsule shells shown in FIGS. 1A, 2A and 3A have been placed; all pieces of capsule shells are dissolved in the McIlvaine's buffer solution of pH 6.8.

Example 2 illustrates that the esterified cellulose ethers of the present invention can be dissolved in water at a high concentration, e.g., at a concentration of 25 wt.-%. The ability to provide highly concentrated solutions of the esterified cellulose ethers of the present invention in water allows efficient and environmentally friendly processes for producing capsule shells or coatings from the esterified cellulose ethers or for producing solid dispersions of drugs in the esterified cellulose ethers at high throughput. Partial neutralization, which might impact the enteric properties of the esterified cellulose ethers, is not needed. Moreover, Example 2 illustrates that the capsules can be prepared even at room temperature.

Moreover, Table 1 above illustrates the low viscosity of the esterified cellulose ethers of the present invention in acetone at 20° C., even at high concentrations. The ability to provide highly concentrated solutions of the esterified cellulose ethers of the present invention in organic solvents such as acetone allows efficient processes for producing capsules or coatings from the esterified cellulose ethers or for producing solid dispersions of drugs in the esterified cellulose ethers at high throughput.

The invention claimed is:

1. An esterified cellulose ether
   i) comprising groups of the formula —C(O)—CH$_2$—CH$_2$—COOH or a combination of acetyl groups and groups of the formula —C(O)—CH$_2$—CH$_2$—COOH,
   ii) having a weight average molecular weight M$_w$ of up to 70,000 Dalton,
   iii) having a degree of neutralization of the groups —C(O)—CH$_2$—CH$_2$—COOH of not more than 0.4, and
   iv) having a solubility in water of at least 2.0 weight percent at 2° C.

2. The esterified cellulose ether of claim 1 having a Polydispersity M$_w$/M$_n$ of not more than 2.0.

3. The esterified cellulose ether of claim 1 having a viscosity of up to 13 mPa·s, measured as a 10 wt.-% solution of the esterified cellulose ether in acetone at 20° C.

4. The esterified cellulose ether of claim 1 wherein at least 85 wt. % of the esterified cellulose ether is soluble in a mixture of 2.5 weight parts of the esterified cellulose ether and 97.5 weight parts of water at 2° C.

5. The esterified cellulose ether of claim 1 wherein at least 85 wt. % of the esterified cellulose ether is soluble in a mixture of 10 weight parts of the esterified cellulose ether and 90 weight parts of water at 2° C.

6. The esterified cellulose ether of claim 1 being hydroxypropyl methyl cellulose acetate succinate.

7. A liquid composition comprising at least one esterified cellulose ether of claim 1 dissolved in an aqueous diluent.

8. A liquid composition comprising at least one esterified cellulose ether of claim 1 and an organic diluent.

9. The liquid composition of claim 7 comprising at least 5 weight percent of the esterified cellulose ether, based on the total weight of the liquid composition.

10. A coated dosage form wherein the coating comprises at least one esterified cellulose ether of claim 1.

11. A polymeric capsule shell comprising at least one esterified cellulose ether of claim 1.

12. A capsule comprising a capsule shell of claim 11 and further comprising a drug or a nutritional or food supplement or a combination thereof.

13. A solid dispersion of at least one active ingredient in at least one esterified cellulose ether of claim 1.

14. The liquid composition of claim 8 comprising at least 5 weight percent of the esterified cellulose ether, based on the total weight of the liquid composition.

* * * * *